United States Patent [19]

Provost et al.

[11] Patent Number: 4,783,407

[45] Date of Patent: Nov. 8, 1988

[54] GROWTH OF HEPATITUS A VIRUS IN VERO CELLS

[75] Inventors: Philip J. Provost, Harleysville; Paula A. Giesa, Lansdale; William J. McAleer, Ambler, all of Pa.

[73] Assignee: Merck & Co., Inc., Rahway, N.J.

[21] Appl. No.: 781,830

[22] Filed: Sep. 30, 1985

[51] Int. Cl.$^4$ .................. C12N 7/00; A61K 39/29
[52] U.S. Cl. ...................................... 435/235; 424/89
[58] Field of Search .................. 435/235, 948, 239; 424/89

[56] References Cited

U.S. PATENT DOCUMENTS 4,164,566  8/1979  Provost et al. ................ 424/89
4,301,249  7/1980  Markus et al. ................ 435/235

FOREIGN PATENT DOCUMENTS 025745  3/1981  European Pat. Off. .

OTHER PUBLICATIONS

Kojima et al., J. of Med. Virol., 7:273–286 (1981).
Locarini et al., J. of Virol., 37:216–225 (1981).
Provost, In Vitro Propagation of Hepatitus A Virus, in Gerety (ed.) Hepatitus A, Academic Press (1984).

*Primary Examiner*—Esther M. Kepplinger
*Attorney, Agent, or Firm*—Jack L. Tribble; Hesna J. Pfeiffer; Donald J. Perrella

[57] ABSTRACT

Hepatitus A virus is grown in Vero cells after passage in in vitro cell culture. Virus replication and continued passage in Vero cells requires extended incubation times, up to about four weeks, for early passages and incubation temperatures no higher than about 32° C. Continued passage results in a significant decrease in incubation time and an increase in virus yield. Cultivation of hepatitus A virus in Vero cells meets the development requirements for an inactivated human vaccine.

8 Claims, No Drawings

GROWTH OF HEPATITUS A VIRUS IN VERO CELLS

BACKGROUND OF THE INVENTION

In vitro growth of hepatitis A virus was first accomplished with virus inocula prepared by prior in vivo passage of hepatitis A virus in certain sub-human primates, Provost et al., U.S. Pat. No. 4,164,566. Subsequently, a procedure was described for the growth of hepatitis A virus in vitro by direct inoculation of cell cultures with human clinical specimens containing the hepatitis A virus, Provost et al., European patent application No. 025745. Hepatitis A virus isolates may be initiated to in vitro growth in cell culture by either of the described techniques. The in vitro cultured hepatitis A virus can then be adapted to growth in several types of cell cultures by serial passages. Such adaptive passaging results in increased hepatitis A virus yields which are absolutely necessary for the development of inactivated viral vaccines. In vitro growth of hepatitis A virus has allowed the adaptation of the virus to growth in cell lines which are acceptable for the production of vaccines, e.g., human fetal diploid lung cells and MRC-5 cells. The MRC-5 cells are suitable for the production of live hepatitis A virus vaccine but are less suitable for inactivated vaccine production. The Vero cell line is more advantageous for the growth of virus in the quantities necessary for inactivated vaccine production. Vero cells are transformed but non-tumorigenic cells derived from cercopithicus monkey kidney, Yasumura et al., Nippon Rinsko 21:1201–1215 (1963). Vero cells are available in larger quantities than are MRC-5 cells and are more readily adaptable to large scale cell culture techniques than are MRC-5 cells.

Attempts to grow hepatitis A virus in Vero cell cultures under conventional growth conditions, e.g., cultivation at about 37° C., have resulted in little or no production of virus particles, Locarnini et al., J. Virology 37:216–225 (1981). The ability to propagate hepatitis A virus in Vero cells would greatly enhance the development of an inactivated vaccine since Vero cells are available in sufficient quantity for mass culture, are considered an acceptable cell substrate for inactivated vaccine production and are technologically advantageous when compared with other acceptable cell lines.

OBJECTS OF THE INVENTION

It is, accordingly, an object of the present invention to provide a commercially feasible method for the large-scale propagation of hepatitis A virus suitable for inactivated vaccine development. Another object is to provide conditions for the successful cultivation of hepatitis A virus in Vero cell cultures. These and other objects of the present invention will be apparent from the following description.

SUMMARY OF THE INVENTION

Hepatitis A virus is grown in Vero cells after passage in in vitro cell culture. Virus replication and continued passage in Vero cells requires extended incubation times, up to about four weeks, for early passages and incubation temperatures no higher than about 32° C. Continued passage results in a significant decrease in incubation time and an increase in virus yield. Cultivation of hepatitis A virus in Vero cells meets the development requirements for human vaccine.

DETAILED DESCRIPTION

The present invention relates to a commercially feasible method for the propagation of hepatitis A virus in continuously cultured Vero cells. The Vero cell line was derived from transformed cercopithecus monkey kidney tissue and has become an acceptable cell line for human vaccine production.

It has now been shown that hepatitis A virus can be grown in Vero cell cultures. Propagation in Vero cells requires a suitable viral inoculum to initiate infection of the Vero cells. The suitable inoculum may include the product of successful infection and growth of the hepatitis A virus in cell cultures, e.g., low passage, normal fetal rhesus monkey kidney-6 cells or transformed rhesus monkey kidney cells, LLC-MK2, at either about 32° C. or about 35° C., or it may be virus-containing clinical specimens, e.g. blood, liver, stool, derived from infected humans or sub-human primates. The Vero cells are used as confluent cell monolayers and may be prepared from a wide range of cell passage levels, e.g., from about 100 to about 200 passages. Any suitable nutrient medium may be used, for example, Eagle's minimal essential medium containing Earle's salts supplemented with about 0.2% to about 0.5% fetal calf serum. Hepatitis A virus inoculum is prepared by freeze-thawing and sonication of cell monolayers to form an infective homogenate.

Typically about 1 part of the homogenized virus infected culture is used as inoculum for from about 100 to about 1000 parts by volume of new cell culture. The inoculated cultures are incubated in an atmosphere of about 5% $CO_2$ in air and at a temperature no higher than about 32° C., typically at from about 29° C. to about 33° C., with about 32° C. being preferred. Hepatitis A virus infected Vero cell monolayers receive fresh nutrient media with fetal calf serum approximately every fifth day following inoculation. All monolayers are periodically fixed and examined for the presence of hepatitis A viral antigen by direct immunofluorescence. Infected cell cultures, cell monolayers plus nutrient medium, are homogenized by freezing-thawing and sonication and examined for antigen by radioimmuno assay. Early passages of the virus require extended incubation times, about 4 weeks, for the development of weakly positive results as determined by both assays.

Hepatitis A virus yields from Vero cells grown in 850 $cm^2$ roller bottles containing about 200 ml of nutrient medium are estimated to be about 20 to about 50 micrograms. When suitably purified and inactivated the antigenic material can be used as a vaccine. In marmoset studies, it has been shown that quantities of formalin-inactivated hepatitis A viral antigen as low as $3 \times 1$ nanogram can immunize against hepatitis A virus infection. Consequently, about 1000 such doses can be prepared from a single roller bottle of Vero cell culture.

Other cell cultures, e.g. low passage fetal rhesus monkey kidney cells, primary African green monkey kidney cells, transformed rhesus monkey kidney cells (LLC-MK2), and human diploid lung fibroblast cells (MRC-5, Wl-38) can all support growth of hepatitis A virus. Yields of hepatitis A virus antigen grown on these cell cultures approximate the yields described for the virus maintained on Vero cells. The Vero cell culture system is unique in that it requires incubation at temperatures no higher than about 32° C. None of the other potential hepatitis A virus substrates have this temperature restriction on viral growth. Also the Vero cell culture system is unique among transformed cells in that is has been accepted as a human vaccine substrate. Thus, the Vero cell line is preferable to other transformed cells such as LLC-MK2. Transformed cells such as the Vero cell line have an infinite lifetime and will always be adequate for large-scale vaccine manufacture. This is the main advantage of the Vero cells over conventional cells such as MRC-5.

EXAMPLE 1

Adaptation of Hepatitis A Virus to Growth in Vero Cells

Hepatitis A virus was isolated and grown in marmosets prior to adaptation to cell culture. Initially, fetal rhesus monkey kidney-6 (FRhK-6) cell culture monolayers were inoculated with hepatitis A virus obtained from an extract of infectious marmoset liver. The homogenized liver was clarified and inoculated, generally 1 part liver extract to from about 20 to 1000 parts by volume of fresh culture fluid to obtain a viral concentration of $2.5 \times 10^5$ infectious dose units per ml. The infected cell cultures were grown at 35° C. in 25 cm$^2$ culture flasks containing 5 ml of a nutrient medium consisting of Eagle's minimal essential media supplemented with 0.5% fetal calf serum. The nutrient medium was replaced at 5 day intervals. Viral growth was shown by various assays for the presence of viral antigens and by the ability to serially passage the viral agent in FRhK-6 cells. Hepatitis A virus for antigen assay and as an inoculum for subsequent cell cultures was released from the cultured cells by twice freezing and thawing the contents of the culture flask and by sonication. This homogenized product was clarified by centrifugation and the supernatant liquid was used to determine viral antigen concentration and as the hepatitis A virus inoculum. A virus homogenate prepared from the eighth serial passage in FRhK-6 cells was used to inoculate LLC-MK2 cells, transformed rhesus monkey kidney, 1 part homogenized cell culture by volume to 20 to 1000 parts Eagle's minimal essential medium by volume to obtain a viral concentration of $2.5 \times 10^5$ infectious dose units per ml. The infected LLC-MK2 cell cultures were maintained under the same conditions as those used for infected FRhK-6 cells except that the fetal calf serum concentration was lowered to 0.2%. Successful growth of hepatitis A virus in LLC-MK2 cell cultures was also demonstrated by various assays for hepatitis A anigen and by the ability to successfully serially transmit the viral infection in LLC-MK2 cells.

Vero cell cultures were inoculated with hepatitis A virus from the fifth serial passage in LLC-MK2 cells. The infected Vero cell cultures received 1 part homogenized cell culture by volume to about 20 to 1000 parts by volume of fresh Eagle's minimal essential medium supplemented with 0.5% fetal calf serum to obtain a viral concentration of $2.5 \times 10^5$ infectious dose units per ml. The initial cultures were incubated at 35° C. in an atmosphere of 5% $CO_2$ in air. Viral growth was severely limited at this temperature and the infection could not be transmitted to other Vero cell cultures at 35° C. When similarly infected Vero cell cultures were incubated at 32° C. viral antigens were detected and infective virus could be passaged. Incubation periods were reduced over the course of about 10 passages from 4 weeks to 2 weeks while viral antigen yields were increased from a trace to about 100 nanograms of hepatitis A virus antigen per millileter of homogenized cell culture.

EXAMPLE 2

Large-Scale Growth of Hepatitis A Virus in Vero Cells

Vero cells were grown to confluency in roller bottles, 850 cm$^2$, under the conditions described in Example 1. The culture fluid was removed and the Vero cell monolayers were inoculated with 15 ml of a 1 to 75 dilution of the homogenized virus product, containing about 20 nanograms of viral antigen, from the eighteenth passage of hepatitis A virus in Vero cells as described in Example 1. The inoculum in fresh nutrient medium was absorbed to the Vero cell culture for about 4 hours at 32° C. and then 185 ml of nutrient medium was added and the roller bottle cultures were incubated at 32° C. The nutrient medium, 200 ml, was replaced at 5 day intervals. The cultures were terminated at day 21 by the homogenization process as in Example 1. In an alternate experiment hepatitis A virus was obtained by discarding the culture fluids and collecting the cell monolayer by scraping and subsequent homogenization. Typical estimates of hepatitis A viral antigen yields per roller bottle culture were about 50 micrograms, representing a 2500-fold increase in viral product over inoculated viral antigen.

What is claimed is:

1. A method of growing hepatitis A virus in cell culture comprising growth of infective virus by passaging at temperatures no higher than 33° C. in Vero cells that have been exposed to an inoculum containing hepatitis A virus until there is a sufficient concentration of virus for vaccine production.

2. A method according to claim 1 wherein the temperature is from about 29° C. to 33° C.

3. A method according to claim 1 wherein the hepatitis A virus inoculum is adapted to grow in Vero cells by at least one passage in a cell culture which supports the growth of hepatitis A virus.

4. A method according to claim 3 wherein the inoculum is adapted for Vero cell culture by growth in fetal rhesus monkey kidney cell culture.

5. A method according to claim 3 wherein the inoculum is adapted for Vero cell culture by growth in transformed rhesus monkey kidney cell culture.

6. A method according to claim 1 wherein the hepatitis A virus inoculum for Vero cell culture is a clinical specimen containing hepatitis A virus.

7. A method according to claim 6 wherein the inoculum is derived from a human or subhuman primate clinical specimen.

8. A method according to claim 1 wherein passaging is at least one passage of the hepatitis A virus in Vero cell culture.

* * * * *